United States Patent [19]

Lafon

[11] 4,107,438
[45] Aug. 15, 1978

[54] CYCLIC PHENYLSULPHINYL-AMIDINE DERIVATIVES

[76] Inventor: Victor Lafon, 76, avenue de la Republique, Paris, France

[21] Appl. No.: 760,407

[22] Filed: Jan. 18, 1977

Related U.S. Application Data

[62] Division of Ser. No. 617,665, Sep. 29, 1975, Pat. No. 4,013,776.

[30] Foreign Application Priority Data

Sep. 30, 1974 [GB] United Kingdom ............ 42387/74

[51] Int. Cl.² ................... C07D 233/22; C07D 239/06
[52] U.S. Cl. ..................................... 548/353; 544/335
[58] Field of Search .................... 260/309.6, 251 R; 424/273, 251; 548/353

[56] References Cited

U.S. PATENT DOCUMENTS

| 3,441,560 | 4/1969 | Zimmermann ................ 260/251 R |
| 3,551,417 | 12/1970 | Symon et al. .................... 260/309.6 |

OTHER PUBLICATIONS

Hoff et al., Chem. Abst. 1972, vol. 76, No. 72513m.
Protiva et al., Chem. Abst. 1948, vol. 42, columns 8188-8189.
Walker Chem. Abst. 1976, vol. 84, No. 2,514,833.

*Primary Examiner*—Natalie Trousof

[57] ABSTRACT

Phenylsulphinyl derivatives of the formula

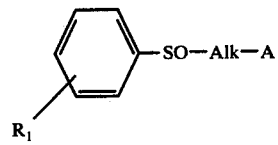

in which $R_1$ represents hydrogen or one or more identical or different substituents, Alk represents a $C_2$-$C_4$ hydrocarbon radical with a linear or branched chain, and A represents $C(=NH)NH_2$, $C(=NH)NHOH$, $C(=O)NHOH$, or

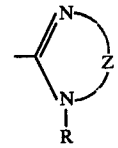

where Z is $CH_2CH_2$ or $CH_2CH_2CH_2$ and R is H, $CH_2COOH$, $CH(CH_3)COOH$ or $C(CH_3)_2COOH$, and their addition salts, have interesting therapeutic properties on the central nervous system as anxiolytic agents and/or analgesic and anti-inflammatory agents.

8 Claims, No Drawings

CYCLIC PHENYLSULPHINYL-AMIDINE DERIVATIVES

This is a division, of application Ser. No. 617,665, filed Sept. 29, 1975, now U.S. Pat. No. 4,013,776.

The present invention relates to phenylsulphinylamidine derivatives and their production.

In the text which follows, "amidines and their derivatives" means compounds which contain an amidino group and also compounds which contain a group derived from, or homologous to, an amidino group, that is to say an amidoxime group, a hydroxamic acid group $C(=O)NHOH$, and cyclic amidino groups such as $2\text{-}\Delta^2$-imidazolinyl and 2-(1,4,5,6-tetrahydro-pyrimidinyl), it being possible for these latter cyclic groups to be substituted.

The compounds of the invention are the phenylsulphinyl-alkyl-amidines and their derivatives of the formula:

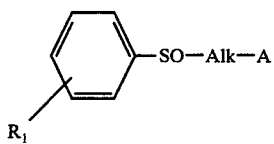   I in which $R_1$ represents hydrogen or one or more identical or different substituents preferably chosen from H, halogen, such as F, Cl and Br, $CF_3$, $C_1$-$C_4$ alkyl, $C_1$-$C_4$ alkoxy, $NO_2$ and methylenedioxy, Alk represents a $C_2$-$C_4$ hydrocarbon radical with a linear or branched chain, and A represents $C(=NH)NH_2$, $C(=NH)NHOH$, $C(=O)NHOH$ or

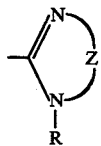

wherein Z is $CH_2CH_2$ or $CH_2CH_2CH_2$ and R is H, $CH_2COOH$, $CH(CH_3)COOH$ or $C(CH_3)_2COOH$, and the addition salts of these compounds. By addition salts are meant ammonium salts and the acid addition salts.

These compounds are useful in therapy, especially as agents which act on the central nervous system as anxiolytic agents and/or analgesic and anti-inflammatory agents.

The compounds of the formula I can be prepared by oxidising a sulphide of the formula

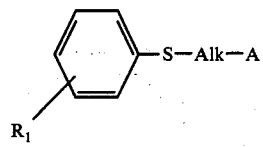   II wherein $R_1$, Alk and A are defined as above, preferably with $H_2O_2$ in the presence of acetic acid.

The oxidation of the sulphide of formula II may be carried out with concentrated hydrogen peroxide, namely hydrogen peroxide of at least 110 volumes strength (that is to say water containing at least 33% by weight of hydrogen peroxide). During this oxidation it is necessary to avoid the formation of a relatively large amount of the corresponding sulphone. In practice, if the reaction is carried out at 100° C for 1 hour or more than 1 hour with hydrogen peroxide of 110–120 volumes strength, essentially only the sulphone is obtained, so that, in order only to obtain the sulphinyl derivative, the reaction is carried out either at 50° C for 1 hour followed by cooling, if necessary, and by maintaining the mixture at ambient temperature (15°–25° C) for several hours (especially from 1 to 3 hours), or at 37°–45° C (the temperature generally reached by the reaction mixture, because the reaction is exothermic), followed by cooling and maintaining the mixture at ambient temperature (15°–25° C) for 3 to 15 hours. Approximately stoichiometric amounts of the sulphide of formula II and $H_2O_2$ can be used.

The acid addition salts, which can be prepared from the bases of the formula I, are obtained by a method which is in itself known, for example by reaction of the free base with an inorganic or organic acid. Amongst the acids which can be used there may in particular be mentioned hydrochloric, hydrobromic, hydriodic, sulphuric, formic, maleic, fumaric, oxalic, ascorbic, citric, acetic, methanesulphonic, p-toluenesulphonic, lactic, succinic, benzoic, salicylic, acetylsalicylic, malic, tartaric, glutamic and aspartic acids.

The preferred compounds of the formula I are those in which $R_1$ is H, F, Cl or $CF_3$, A is $-C(=NH)NH_2$, $-C(=NH)NHOH$, $-C(=O)NHOH$ or

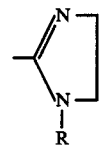

and Alk is $(CH_2)_2$ or $(CH_2)_3$.

The sulphides of the formula II (which are new) can be prepared by various reaction methods from an optionally substituted thiophenol, as illustrated in scheme I which follows:

SCHEME I

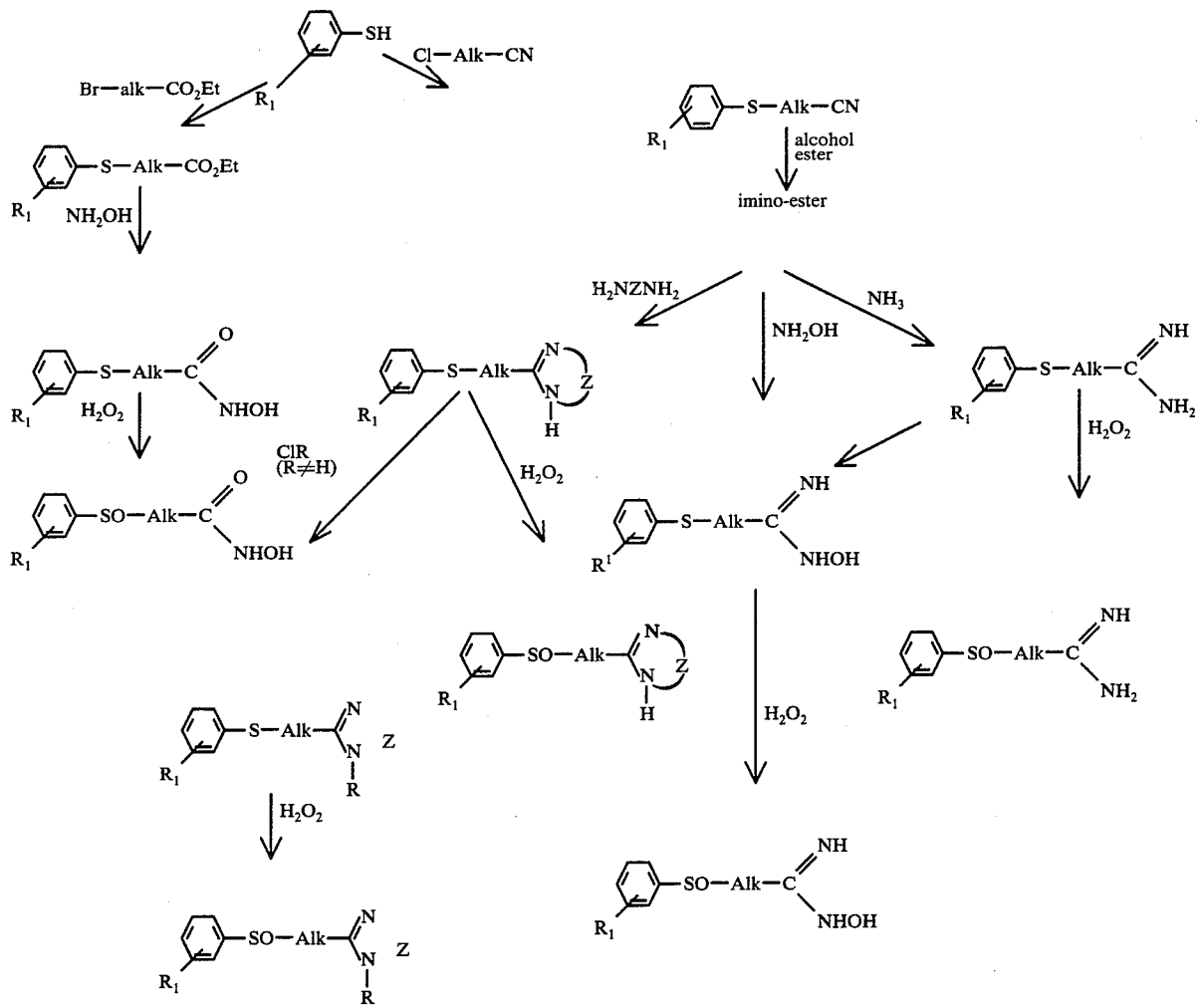

Of course the reactions of scheme I can be modified in accordance with the requirements of each synthesis. Thus, it is not necessary to isolate the imino-ester obtained from the phenylthioalkylnitrile in order to prepare the amidines, amidoximes and cyclic amidines; instead, the said imino-ester can be formed in situ. Furthermore, the reaction which consists of introducing a group R (different from H) into the 1-position of the cyclic amidino group can be carried out with a halogen derivative other than ClR, and for example BrR can be used.

The following Examples illustrate the invention. In these Examples the temperatures are expressed in degrees C, the term ether without additional definition denotes diethyl ether and conversely if the ether is specified it is a different product (thus, the expression isopropyl ether denotes diisopropyl ether).

All the products described in the Examples are listed in the tables given below. Table I relates to the cyclic amidino derivatives, and Table II relates to the derivatives wherein $A = C(=NH)NH_2$, $C(=NH)NHOH$ and $C(=O)NHOH$. Tables I bis and II bis relate to the intermediate sulphides II which are involved, respectively, in the synthesis of the compounds of Tables I and II.

TABLE I

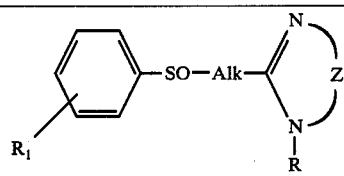

| Example | $R_1$ | Alk | Z | R | Base or acid addition salt | Melting point, °C | Code No. |
|---|---|---|---|---|---|---|---|
| 1 | 4-Cl | $CH_2CH_2$ | $CH_2CH_2$ | H | HCl | 142–144 | CRL 40,065 |
| 2 | 3-$CF_3$ | $CH_2CH_2$ | $CH_2CH_2$ | H | HCl | 109–110 | CRL 40,094 |
| 3 | H | $CH_2CH_2$ | $CH_2CH_2$ | $CH_2COOH$ | Free base | 110–112 | CRL 40,111 |
| 4 | 4-Cl | $CH_2CH_2$ | $CH_2CH_2$ | $CH_2COOH$ | Free base | 132–133 | CRL 40,112 |
| 5 | 4-Cl | $CH_2CH_2$ | $CH_2CH_2$ | $CH(CH_3)COOH$ | Free base | 119–120 | CRL 40,113 |

TABLE I-continued

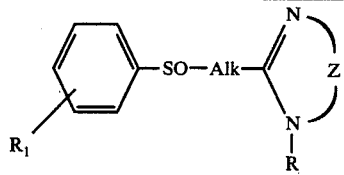

| Example | R₁ | Alk | Z | R | Base or acid addition salt | Melting point, °C | Code No. |
|---|---|---|---|---|---|---|---|
| 6 | H | CH₂CH₂ | CH₂CH₂ | H | HCl | 115–116 | CRL 4,019 |

Table I bis

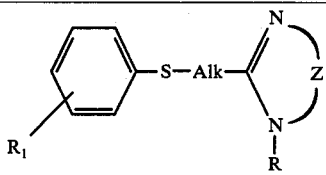

| Intermediate products | R₁ | Alk | Z | R | Base or acid addition salt | Melting point °C |
|---|---|---|---|---|---|---|
| A-1 | 4-Cl | CH₂CH₂ | CH₂CH₂ | H | HCl | 130–132 |
| A-2 | 3-CF₃ | CH₂CH₂ | CH₂CH₂ | H | HCl | 137 |
| A-3 | H | CH₂CH₂ | CH₂CH₂ | CH₂COOH | Free base | 60–62 |
| A-4 | 4-Cl | CH₂CH₂ | CH₂CH₂ | CH₂COOH | Free base | 98–99 |
| A-5 | 4-Cl | CH₂CH₂ | CH₂CH₂ | CH(CH₃)COOH | Free base | 92–93 |
| A-6 | H | CH₂CH₂ | CH₂CH₂ | H | HCl | 128–130 |

TABLE II

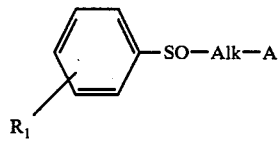

| Example | R₁ | Alk | A | Base or acid addition salt | Melting point °C | Code No. |
|---|---|---|---|---|---|---|
| 7 | 4-F | CH₂CH₂CH₂ | C(=NH)NHOH | HCl | 186–188 | CRL 40,218 |
| 8 | 4-F | CH₂CH₂ | C(=NH)NHOH | HCl | 146–148(dec) | CRL 40,220 |
| 9 | 4-Cl | CH₂CH₂CH₂ | C(=NH)NHOH | HCl | 178–80 | CRL 40,266 |
| 10 | 4-F | CH₂CH₂CH₂ | C(=NH)NH₂ | HCl | 138 | CRL 40,267 |
| 11 | H | CH₂CH₂CH₂ | C(=NH)NHOH | HCl | 152 | CRL 40,268 |
| 12 | H | CH₂CH₂CH₂ | C(=O)NHOH | Free base | 61–62 | CRL 40,216 |
| 13 | 4-F | CH₂CH₂CH₂ | C(=O)NHOH | Free base | 109–110 | CRL 40,217 |
| 14 | 4-F | CH₂CH₂ | C(=O)NHOH | Free base | 133 | CRL 40,219 |
| 15 | 4-Cl | CH₂CH₂CH₂ | C(=O)NHOH | Free base | 126–127 | CRL 40,265 |

TABLE II bis

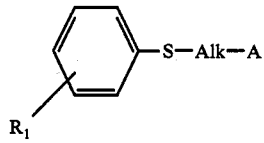

| Intermediate product | R₁ | Alk | A | Base or acid addition salt | Melting point °C |
|---|---|---|---|---|---|
| A-7 | 4-F | CH₂CH₂CH₂ | C(=NH)NHOH | Free base | 104 |
|  |  |  |  | HCl | 75–76 |
| A-8 | 4-F | CH₂CH₂ | C(=NH)NHOH | Free base | 86 |
|  |  |  |  | HCl | 136–138 |
| A-9 | 4-Cl | CH₂CH₂CH₂ | C(=NH)NHOH | Free base | 99 |
|  |  |  |  | HCl | 88–89 |
| A-10 | 4-F | CH₂CH₂CH₂ | C(=NH)NH₂ | HCl | 71 |
| A-11 | H | CH₂CH₂CH₂ | C(NH)NHOH | Free base | 90–91 |
|  |  |  |  | HCl | 77–78 |
| A-12 | H | CH₂CH₂CH₂ | C(=O)NHOH | Free base | 78–79 |
| A-13 | 4-F | CH₂CH₂CH₂ | C(=O)NHOH | Free base | 96 |
| A-14 | 4-F | CH₂CH₂ | C(=O)NHOH | Free base | 93 |
| A-15 | 4-Cl | CH₂CH₂CH₂ | C(=O)NHOH | Free base | 76–77 |

EXAMPLE 1

2-[2-(p-Chlorophenylsulphinyl)-ethyl]-Δ²-imidazoline hydrochloride

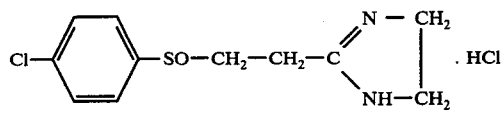

Code No. CRL 40,065 a. 3-(p-Chlorophenylthio)-propionitrile 10 ml of β-chloropropionitrile (0.13 mol) are added, whilst stirring at 70°–80° C, to a solution of 17.4 g (0.12 mol) of p-chlorothiophenol and 4.8 g of sodium hydroxide pellets in 50 ml of water. The mixture is kept at 80° C for half an hour. After cooling, it is extracted with ether and the extract is washed with water and dried. 22.5 g of 3-(p-chlorophenylthio)-propionitrile. Melting point = 53–54° C.

b. 2-[2-(p-Chlorophenylthio)-ethyl]-Δ²-imidazoline hydrochloride

A solution of 22.5 g (0.114 mol) of 3-(p-chlorophenylthio)-propionitrile in 200 ml of ether and 12 ml of ethanol is saturated with dry HCl gas. The reactants are left in contact at +5° C for 48 hours and the product is then filtered off. 20 g of the imino-ester hydrochloride are obtained. Melting point = 108°–110° C.

4.2 g (0.07 mol) of ethylenediamine are added to 19 g (0.068 mol) of the said iminoester hydrochloride dissolved in 100 ml of ethanol, and the mixture is heated to the reflux temperature for 2 hours. It is then evaporated to dryness in vacuo, the residue is taken up in water and concentrated HCl is added until the pH is 1. The mixture is filtered through charcoal and the product is precipitated in the cold with concentrated NaOH. It is filtered off, washed with water and dried. 14.5 g of free base are obtained; melting point = 68°–70° C. This base is converted to the hydrochloride; melting point = 130°–132° C.

c. CRL 40,065

3.2 ml (0.032 mol) of hydrogen peroxide of 110 volumes strength are added to a solution of 8.9 g of 2-[2-(p-chlorophenylthio)-ethyl]-Δ²-imidazoline hydrochloride in 30 ml of acetic acid. After 1 hour at 50° C and standing overnight, the mixture is evaporated to dryness in vacuo. The residue is taken up in acetone, filtered off and recrystallised from isopropanol. CRL 40,065 is obtained in a yield of 40%. It is in the form of small white needles melting at 142°–144° C. It is soluble in water and ethanol and insoluble in acetone and ether.

EXAMPLE 2

2-[2-(Meta-trifluoromethylphenylsulphinyl)-ethyl]-Δ²-imidazoline hydrochloride

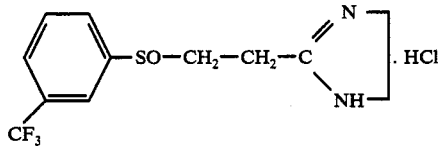

Code No. CRL 40,094 a. 3-(3-Trifluoromethylphenylthio)-propioniminoethyl ester hydrochloride.

A solution of 15.9 g (0.09 mol) of 3-trifluoromethylthiophenol and 3.8 g (0.095 mol) of sodium hydroxide pellets in 100 ml of water is heated at 65°–70° C and 8.5 g (0.095 mol) of β-chloropropionitrile are added dropwise whilst stirring. The mixture is heated for a quarter of an hour to the reflux temperature and is then cooled and extracted with ether, and the extract is washed with water and dried with magnesium sulphate. This gives 3-(3-trifluoromethylphenylthio)-propionitrile, which is not isolated.

The magnesium sulphate is filtered off, 10 ml of ethanol are added to the filtrate and the mixture is saturated with dry HCl gas at 0° C. It is then left to stand for 48 hours and the product is filtered off. 25.6 g (90%) of the expected iminoethyl ester hydrochloride are obtained. Melting point = 92° C.

b. 2-[2-(3-Trifluoromethylphenylthio)-ethyl]-Δ²-imidazoline hydrochloride.

4.8 g (5.4 ml; 0.08 ml) of ethylenediamine are added to a solution of 25 g (0.08 mol) of 2-(m-trifluoromethylphenylthio)-propioniminoethyl ester hydrochloride in 100 ml of ethanol. The mixture is heated to the reflux temperature for 2 hours and is then evaporated to dryness in vacuo, and the residue is taken up in water with a few drops of concentrated HCl. The mixture is filtered through charcoal and the base is precipitated with concentrated NaOH, filtered off, washed with water and dried. This gives 16.3 g of the free base. Melting point = 71°–72° C. The base is dissolved in ethyl acetate, the solution is filtered through charcoal, a solution of hydrogen chloride in ethanol is added to the filtrate and the product is filtered off. 16.4 g (66%) are obtained. Melting point = 137° C.

c. CRL 40,094

5.2 ml (0.052 mol) of hydrogen peroxide of 110 volumes strength are added to a solution of 16.2 g (0.052 mol) of the hydrochloride obtained above in 50 ml of acetic acid. The temperature of the mixture rises, and the mixture is kept at 50° C for 1 hour and is then evaporated to dryness in vacuo. The residue is taken up with 100 ml of water and the mixture is filtered through charcoal and evaporated to dryness in vacuo. 100 ml of ethyl acetate are added and the product is filtered off and recrystallised from acetone. CRL 40,094 is obtained in a yield of 44%. It is in the form of small cream-coloured flakes. It is soluble in water and alcohols, sparingly soluble in cold acetone and insoluble in ether and ethyl acetate. It melts at 109°–110° C.

EXAMPLE 3

{2-[2-(Phenylsulphinyl)-ethyl]-Δ²-imidazolin-1-yl}-acetic acid

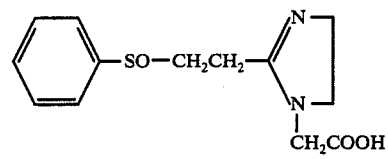

Code No. CRL 40,111

A suspension of 10.4 g of 2-[2-(phenylthio)-ethyl]-Δ²-imidazoline (0.05 mol) and 10.6 g (0.1 mol) of sodium carbonate in 50 ml of water is heated to 70°–80° C, 5 g (0.053 mol) of chloroacetic acid dissolved in 10 ml of water are added whilst stirring and the mixture is neutralised with sodium carbonate. It is heated to 80° C for a further 10 minutes whilst stirring. The cold solution is acidified with concentrated HCl. The product is filtered off and washed with a little cold water. This gives {2-[2-(phenylthio)-ethyl]-Δ²-imidazolin-1-yl}-acetic acid in a yield of 70%. Melting point = 62°-63° C.

15.6 g of this acid (0.06 mol) dissolved in 60 ml of acetic acid are oxidised with 6 ml of hydrogen peroxide of 110 volumes strength. The mixture is evaporated to dryness in vacuo and the residue is taken up in isopropyl ether and filtered off. This gives CRL 40,111 in a yield of 60%. Melting point = 110°-112° C.

EXAMPLE 4

{2-[2-(p-Chlorophenylsulphinyl)-ethyl]-Δ²-imidazolin-1-yl}-acetic acid

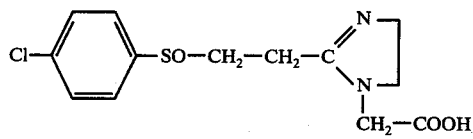

Code No. CRL 40,112

A solution of 4 g (0.042 mol) of chloroacetic acid and 5 g (0.05 mol) of sodium carbonate is added dropwise to a suspension, at 70°-80° C, of 9.6 g (0.04 mol) of 2-[2-(p-chlorophenylthio)-ethyl]-Δ²-imidazoline and 8.5 g (0.08 mol) of Na₂CO₃ in 50 ml of water. The mixture is heated to 80° C for a further 10 minutes. The solution is then cooled and acidified with concentrated HCl. The product is filtered off, washed with cold water and dried. This gives {2-[2-p-chlorophenylthio)-ethyl]-Δ²-imidazolin-1-yl}-acetic acid. Melting point = 98°-99° C.

12 g (0.04 mol) of this acid dissolved in 40 ml of acetic acid are oxidised with 4 ml of hydrogen peroxide of 110 volumes strength. The mixture is evaporated to dryness in vacuo and the residue is taken up in cold water, filtered off, dried and washed with a little isopropyl ether. It is recrystallised from isopropanol. This gives CRL 40,112, in a yield of 56%. Melting point = 132°-133° C.

EXAMPLE 5

α-{2-[2-(p-Chlorophenylsulphinyl)-ethyl]-Δ²-imidazolin-1-yl}-propionic acid.

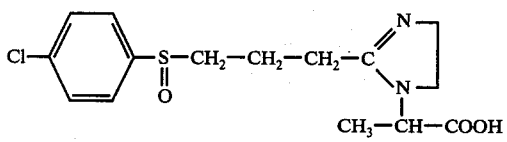

A suspension of 12 g (0.05 mol) of 2-[2-(p-chlorophenylthio)-ethyl]-Δ²-imidazoline and 10.6 g (0.1 mol) of sodium carbonate in 60 ml of water is heated to 70°-80° C and a solution of 8 g (0.052 mol) of α-bromopropionic acid and 5.4 g (0.052 mol) of sodium carbonate in 20 ml of water is added whilst stirring; the mixture is kept at 80° C for 10 minutes and is then cooled and precipitated with concentrated HCl. The product is filtered off, washed with water and dried. α-{2-[2-(p-Chlorophenylthio)-ethyl]-Δ²-imidazolin-1-yl}-acetic acid is obtained. Melting point = 92°-93° C.

9.5 g (0.031 mol) of this acid dissolved in 30 ml of acetic acid are oxidised with 3.1 ml (0.031 mol) of hydrogen peroxide of 110 volumes strength. After 1 hour at 50° C, the mixture is evaporated to dryness in vacuo, the residue is taken up with dilute sodium bicarbonate, the mixture is filtered and the product is precipitated with concentrated HCl, filtered off and dried. It is recrystallised from a mixture of ethyl acetate and petroleum ether (50 : 50). This gives CRL 40,113, in a yield of 50%. Melting point = 119°-120° C.

EXAMPLE 6

2-[2-(Phenylsulphinyl)-ethyl]-Δ²-imidazoline hydrochloride.

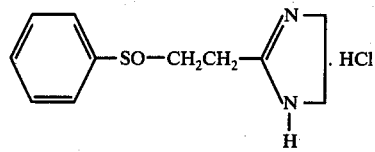

Code No. CRL 4,019 a. 2-[2-(Phenylthio)-ethyl]-Δ²-imidazoline hydrochloride

A solution of 13.2 g (0.12 mol) of thiophenol and 4.8 g (0.12 mol) of NaOH in 100 ml of water is heated to 80° C and 10 ml (0.13 mol) of β-chloropropionitrile is added. The mixture is stirred for a further 10 minutes at 80° C and is then left to cool. It is extracted with twice 100 ml of ether and the ether is washed with dilute sodium hydroxide solution, dilute HCl and water, and dried. 8 ml of ethanol are added to this solution in ether, the mixture is saturated with dry HCl gas. The reactants are left in contact in the cold for 48 hours and the mixture is then evaporated in vacuo.

The residue (30 g) is dissolved in 90 ml of ethanol, 10 ml of ethylenediamine are added and the mixture is heated to the reflux temperature for 2 hours. The precipitate of ethylenediamine hydrochloride is filtered off and the filtrate is evaporated to dryness in vacuo; the residue is taken up in dilute hydrochloric acid, the solution is extracted with ether, and the product is precipitated by means of concentrated sodium hydroxide solution, filtered off and dried. The hydrochloride is obtained by treating the base (melting point = 80° C) dissolved in ethyl acetate, with a solution of hydrogen chloride in ethanol. This gives 22 g of 2-[2-(phenylthio)-ethyl]-Δ²-imidazoline hydrochloride; yield 75%; melting point = 128°-130° C.

b. CRL 4,019

12.1 g (0.05 mol) of the above hydrochloride, dissolved in 50 ml of acetic acid, are oxidised with 5 ml (0.05 mol) of hydrogen peroxide. The mixture is evaporated to dryness in vacuo and the residue is taken up in acetone and filtered off. The precipitate is taken up in the minimum amount of slightly acid water, the solution is filtered and evaporated in vacuo and the residue is recrystallised from a mixture of ethanol and acetone. 2-[2-(phenylsulphinyl)-ethyl]-Δ²-imidazoline hydrochloride is obtained in a yield of 55%. It is in the form of "creamy white" very hygroscopic crystals. Melting point = 115°-116° C.

EXAMPLE 7

4-p-Fluorophenylsulphinyl-butyramidoxime hydrochloride.

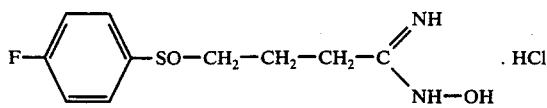

Code No.: CRL 40,218 a. 4-p-Fluorophenylthio-butyramidoxime hydrochloride

A solution of 10 g (0.078 mol) of p-fluorothiophenol and 3.2 g (0.08 mol) of sodium hydroxide pellets in 100 ml of water is heated to 70° C. 8.3 g (0.08 mol) of γ-chlorobutyronitrile are added dropwise, whilst stirring. After 10 minutes under reflux and standing for 1 hour, the mixture is extracted with ether and the extract is washed with water, dried and evaporated in vacuo. A solution of hydroxylamine prepared from 10.5 g (0.15 mol) of hydroxylamine hydrochloride, 15 g of potassium bicarbonate in 15 ml of water and 60 ml of butanol is added to the residue. The mixture is heated for 3 hours to the reflux temperature, whilst stirring. After standing overnight, the base is filtered off and 11 g of product are obtained. Melting point = 104° C.

The hydrochloride is obtained by acidifying a solution of the base in ethyl acetate with a solution of hydrogen chloride in ethanol. Melting point = 75°–76° C.

b. CRL 40,218

11.15 g (0.042 mol) of 4-p-fluorophenylthiobutyramidoxime hydrochloride dissolved in 42 ml of acetic acid are oxidised by means of 4.2 ml of hydrogen peroxide of 110 volumes strength. After the initial rise in temperature, the reactants are left in contact for 3 hours and the mixture is evaporated to dryness in vacuo. The residue is taken up with 50 ml of acetone and filtered off. CRL 40,218 is obtained in a yield of 55%. It is in the form of small white crystals. It is soluble in water and the alcohols and insoluble in acetone, ether and benzene. It melts at 186°–188° C.

EXAMPLE 8

3-p-Fluorophenylsulphinyl-propionamidoxime hydrochloride.

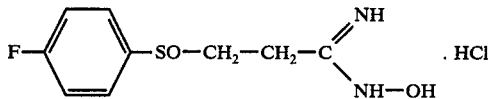

Code No.: CRL 40,220 a. 3-p-Fluorophenylthio-propionamidoxime hydrochloride

A solution of 10 g (0.078 mol) of p-fluorothiophenol and 3.2 g (0.08 mol) of sodium hydroxide pellets in 100 ml of water is heated to 70° C whilst stirring and 8 g (0.09 mol) of β-chloropropionitrile are added dropwise. The mixture is further heated to the reflux termperature for 10 minutes and after cooling it is extracted with ether and the extract is washed with water, dried, and evaporated. The ester thus obtained, dissolved in 50 ml of butanol, is heated for 4 hours to the reflux temperature with a solution of hydroxylamine prepared from 7 g (0.1 mol) of hydroxylamine hydrochloride, 10 g of potassium bicarbonate and 15 ml of water. The mixture is then acidified with concentrated HCl and evaporated to dryness in vacuo. The residue is taken up with water, the mixture is extracted with ether, the ether phase is discarded, the aqueous phase is filtered through charcoal and the base is precipitated by means of sodium carbonate. It is filtered off, washed with water and dried. 10.1 g of product are obtained. Melting point = 86° C.

The hydrochloride (melting point = 136°–138°) is obtained by acidifying a solution of the base in ethyl acetate with a solution of hydrogen chloride in ethanol.

b. CRL 40,220

11.5 g (0.046 mol) of 3-p-fluorophenylthio-propionamidoxime hydrochloride dissolved in 46 ml of acetic acid are oxidised with 46 ml of hydrogen peroxide of 110 volumes strength. After the initial temperature rise (about 40° C), the mixture is left to stand for 2 hours and is evaporated to dryness in vacuo and the residue is taken up in acetone, filtered off and recrystallised from methanol. CRL 40,220 is obtained in a yield of 58%. This product is in the form of small white crystals melting, with decomposition, at 146°–148° C.

EXAMPLE 9

4-(p-Chlorophenylsulphinyl)-butyramidoxime hydrochloride.

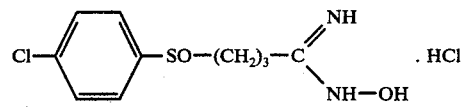

Code No.: CRL 40,266 a. 4-(p-Chlorophenylthio)-butyramidoxime hydrochloride

A stirred mixture of 29 g (0.2 mol) of p-chlorothiophenol and 8 g of sodium hydroxide pellets in 200 ml of water is heated to 80° C. 22 g (0.21 mol) of γ-chlorobutyronitrile are added dropwise and the mixture is heated to the reflux temperature for a quarter of an hour. It is then cooled and extracted with methylene chloride, and the extract is washed with water, dried and evaporated to dryness in vacuo. The residual oil, namely 42 g (0.2 mol), dissolved in 180 ml of butanol, is added to a solution of 21 g (0.3 mol) of hydroxylamine hydrochloride and 30 g of potassium bicarbonate in 40 ml of water. The mixture is heated to the reflux temperature for 5 hours and the butanol is evaporated in vacuo. 1 liter of water is added, and the product is filtered off, washed with water and then with twice 50 ml of isopropyl ether, dried and recrystallised from isopropanol.

34.5 g of base (melting point = 99° C) are obtained and are converted to the hydrochloride by adding a solution of hydrogen chloride in ether to the solution of the base in ethyl acetate. 38 g (68%) of hydrochloride are obtained. Melting point = 88°–89° C.

b. CRL 40,226

20.5 g (0.075 mol) of the above hydrochloride, dissolved in 75 ml of acetic acid, are oxidised with 6.9 ml of hydrogen peroxide of 120 volumes strength for 1 hour at 50° C. After standing overnight, the mixture is evaporated to dryness in vacuo, and the residue is taken up in acetone, filtered off and recrystallised from propanol. CRL 40,266, which is in the form of a white powder, is obtained in a yield of 58%. Melting point = 178°–180° C.

EXAMPLE 10

4(Para-fluorophenylsulphinyl)-butyramidine hydrochloride

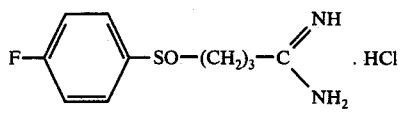

Code No. CRL 40,267 a. 4-(p-Fluorophenylthio)-butyroiminoethyl ester hydrochloride

A solution of 14.5 g (0.075 mol) of 4-(p-fluorophenyl-thio)-butyronitrile and 8 ml of ethanol in 75 ml of ether is saturated with dry HCl gas at 0° C. The mixture is kept in the cold for 24 hours and the product is then filtered off and washed with ether. 17 g (yield 82%) of the iminoethyl ester are obtained. Melting point = 103°–104° C.

b. 4-(p-Fluorophenylthio)-butyramidine hydrochloride 17 g (0.061 mol) of the hydrochloride of the above iminoester dissolved in 100 ml of ethanol are saturated in the cold (at about 0° C) with dry NH₃ gas, the reactants are left in contact for 24 hours, the alcohol is evaporated in vacuo and the residue is taken up in 100 ml of ether and filtered off. 15 g of the sulphide (yield 96%) are obtained. Melting point = 71° C.

c. CRL 40,267

15 g (0.06 mol) of 4-(p-fluorophenylthio)-butyramidine hydrochloride dissolved in 50 ml of acetic acid are oxidised with 5.6 ml of hydrogen peroxide of 120 volumes strength in 1 hour at 50° C. The mixture is left to stand overnight and is then evaporated in vacuo and the residue is taken up in acetone, filtered off and recrystallised from isopropanol. CRL 40,267 is obtained in a yield of 76%; it is in the form of small white crystals. Melting point = 138° C.

EXAMPLE 11

4-(Phenylsulphinyl)-butyramidoxime hydrochloride

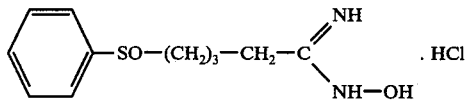

Code No. CRL 40,268 a. 4-(Phenylthio)-butyramidoxime hydrochloride 22 g (0.21 mol) of γ-chlorobutyronitrile are added dropwise to a stirred solution, at 80° C, of 22 g (0.2 mol) of thiophenol and 8 g (0.2 mol) of NaOH in 200 ml of water. The mixture is heated to the reflux temperature for a quarter of an hour and is then cooled and extracted with methylene chloride and the extract is washed with water, dried and evaporated.

The residual oil, which consists of 35.4 g (0.2 mol) of 4-phenylthiobutyronitrile, is dissolved in 180 ml of butanol and added to a solution of hydroxylamine (0.3 mol) in 40 ml of water. The mixture is heated to the reflux temperature for 4 hours and is then evaporated in vacuo, 1 liter of water is added and the product is filtered off and washed with water and then with isopropyl ether. The free base (melting point = 90°–91° C) is obtained. This base, dissolved in ethyl acetate, is converted to the hydrochloride by adding a solution of hydrogen chloride in ethanol. 22 g (44% yield) are obtained. Melting point = 77°–78° C.

b. CRL 40,268

18.5 g (0.075 mol) of the above hydrochloride, dissolved in 75 ml of acetic acid, are oxidised with 7 ml of hydrogen peroxide of 120 volumes strength. The acetic acid is evaporated in vacuo and the residue is taken up in 100 ml of acetone and filtered off. It is recrystallised from a mixture of ethanol and acetone and CRL 40,268 is obtained in a yield of 38%. This product is in the form of a white powder. Melting point = 152° C.

EXAMPLE 12

4-Phenylsulphinyl-butyrohydroxamic acid

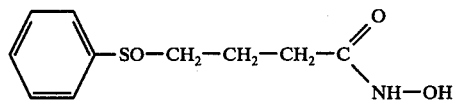

Code No. CRL 40,216 a. 4-Phenylthio-butyrohydroxamic acid 8.1 ml (0.078 mol) of thiophenol and 15.6 g (0.08 mol) of ethyl γ-bromobutyrate in 50 ml of ethanol are mixed, 3.2 g of sodium hydroxide in 40 ml of water are added, after the initial temperature rise the mixture is left to stand for 1 hour, the alcohol is evaporated, the residue is extracted with ether, the extract is washed with water and dried, and the ether is evaporated in vacuo. The ester thus obtained is poured into a solution of hydroxylamine prepared in the cold from 7 g (0.1 mol) of hydroxylamine hydrochloride and 10.8 g (0.2 mol) of sodium methylate in 100 ml of methanol. After leaving the reactants in contact for 48 hours, the mixture is evaporated to dryness in vacuo. The residue is taken up in 200 ml of water, the mixture is filtered through charcoal, the filtrate is precipitated with concentrated HCl and the product is filtered off and dried. It is recrystallised from isopropanol. 8 g (66%) are obtained. Melting point = 78°–79° C.

b. CRL 40,216

7.6 g (0.036 mol) of 4-phenylthio-butyrohydroxamic acid dissolved in 36 ml of acetic acid are oxidised with 3.6 ml (0.036 mol) of hydrogen peroxide of 110 volumes strength. The mixture is evaporated to dryness in vacuo and the water is driven off by taking up the residue in anhydrous ethanol and evaporating, this procedure being repeated several times. The product is crystallised from ethyl acetate. CRL 40,216 is thus obtained in a yield of 38%. This product is in the form of small beige crystals. Melting point = 61°–62° C.

EXAMPLE 13

4-(p-Fluorophenylsulphinyl)-butyrohydroxamic acid

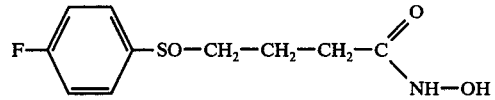

Code No. CRL 40,217 a. 4-(p-Fluorophenylthio)-butyrohydroxamic acid 10 g (0.078 mol) of p-fluorothiophenol are added at 0° C to a solution of 4.3 g (0.08 mol) of sodium methylate in 25 ml of methanol, the mixture is stirred and a solution of 15.6 g (0.08 mol) of ethyl γ-bromobutyrate in 20 ml of methanol is added dropwise at 20° C. The temperature of the mixture reaches 40° C at the end of the addition. The mixture is heated for 2 hours to the reflux temperature and is then evaporated to dryness in vacuo, the residue is extracted with ether and the extract is washed with dilute sodium hydroxide solution and with water, dried and evaporated in vacuo.

A solution of 7 g (0.1 mol) of hydroxylamine hydrochloride in 100 ml of methanol is prepared, a cold solution of 10.8 g (0.2 mol) of sodium methylate in 40 ml of methanol is added at about 10° C, the mixture is filtered and 18 g (0.075 mol) of ethyl 4-(p-fluorophenylthio)-butyrate are added; the reactants are left in contact for 24 hours, the mixture is evaporated to dryness in vacuo, the residue is taken up in 250 ml of water, the solution is filtered through charcoal and the product is precipitated with concentrated HCl. It is filtered off, washed with water, dried and recrystallised from ethyl acetate. 12.8 g (74%) are obtained. Melting point = 96° C.

b. CRL 40,217

10.5 g (0.046 mol) of 4-(p-fluorophenylthio)-butyrohydroxamic acid dissolved in 45 ml of acetic acid are oxidised with 4.6 ml of hydrogen peroxide of 110 volumes strength. After 1 hour at 50° C, the mixture is left to stand overnight and is then evaporated to dryness in vacuo. The residue is taken up in ethyl acetate and filtered off.

CRL 40,217 is obtained in a yield of 62%. It is in the form of small beige crystals. Melting point = 109°–110° C.

EXAMPLE 14

3-(p-Fluorophenylsulphinyl)-propiohydroxamic acid

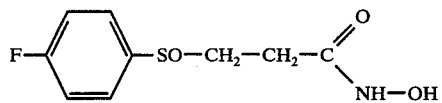

Code No.: CRL 40,219 a. 3-(p-Fluorophenylthio)-propiohydroxamic acid 10 g (0.078 mol) of p-fluorothiophenol are added to a solution of 4.5 g (0.083 mol) of sodium methylate in 25 ml of methanol, and a solution of 14.5 g (0.08 mol) of ethyl 3-bromopropionate in 20 ml of methanol is then added dropwise. The mixture is heated for 2 hours to the reflux temperature, the alcohol is evaporated in vacuo, the residue is taken up in ether, the ether solution is washed with water and dried, and the ether is evaporated. The residue is treated, for 24 hours at 20° C, with a solution of hydroxylamine in methanol prepared from 7.7 g (0.11 mol) of hydroxylamine hydrochloride and 12 g (0.22 mol) of sodium methylate in 150 ml of methanol. The methanol is evaporated in vacuo, 200 ml of water are added, the mixture is extracted with ether and the hydroxamic acid is precipitated with concentrated HCl. It is filtered off, washed with water and dried. 10 g (62%) are obtained. Melting point = 93° C.

b. CRL 402,19

9.85 g (0.046 mol) of 3-(p-fluorophenylthio)-propiohydroxamic acid dissolved in 46 ml of acetic acid are oxidised by adding 4.6 ml of hydrogen peroxide of 110 volumes strength. The reactants are left in contact for 3 hours, the mixture is evaporated to dryness in vacuo, the residue is taken up in ethyl acetate and the product is filtered off and recrystallised from ethanol.

CRL 40,219 is obtained in a yield of 52%. This product is in the form of small white crystals. Melting point = 133° C.

EXAMPLE 15

4-(p-Chlorophenylsulphinyl)-butyrohydroxamic acid

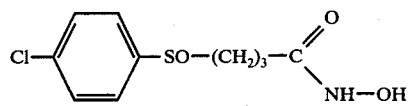

Code No. CRL 40,265 a. Ethyl 4-(p-chlorophenylthio)-butyrate 14.5 g (0.1 mol) of p-chlorothiophenol are added at 0° C to a solution of 5.4 g (0.1 mol) of sodium methylate in 50 ml of methanol and thereafter 19.5 g (0.1 mol) of ethyl γ-bromobutyrate dissolved in 40 ml of methanol are added dropwise at 20° C, whilst stirring. The mixture is heated for 2 hours to the reflux temperature and is then evaporated in vacuo, the residue is extracted with ether, the extract is washed with water and dried, and the ether is evaporated. 24 g (93%) of a white oil are obtained.

b. 4-(p-Chlorophenylthio)-butyrohydroxamic acid

A solution of hydroxylamine is prepared from 10.5 g (0.15 mol) of hydroxylamine hydrochloride dissolved in 150 ml of methanol, to which is added a solution of 13.5 g (0.25 mol) of sodium methylate in 100 ml of methanol. The sodium chloride is filtered off and 24 g (0.092 mol) of ethyl 4-(p-chlorophenylthio)-butyrate are added to the filtrate. The reactants are left in contact for 24 hours, the alcohol is evaporated in vacuo, the residue is taken up in 250 ml of water, the mixture is filtered and the acid is precipitated with concentrated HCl. The product is filtered off, washed with water, dried and recrystallised from benzene. 22 g (96%) of product are obtained. Melting point = 76°–77° C.

c. CRL 40,265

8 ml of hydrogen peroxide of 110 volumes strength are added to a solution of 19.6 g (0.08 mol) of the preceding sulphide in 80 ml of acetic acid. After 1 hour at 50° C and standing ovrnight, the mixture is evaporated in vacuo, 100 ml of ethyl acetate are added and the product is filtered off and recrystallised from ethanol. This gives CRL 40,265 in a yield of 80%; it is in the form of fine white needles. Melting point = 126°–127° C.

The compounds according to the invention are useful in therapy, especially as analgesic and anti-inflammatory agents and/or substances which act on the central nervous system. All of them as analgesic agents, the intensity of the analgesic action varying according to the product. Some of these products exhibit other interesting properties alongside the analgesic effect. Thus the product of Example 6 (CRL 4,019), which has an LD-50 of 350 mg/kg on oral administration to mice, also acts as an antiinflammatory agent in the carragenin oedema test and the product of Example 7 (CRL 40,218) is a stimulant of the central nervous system and acts as an anxiolytic agent. The products of Examples 12, 13 and 14 are active on the central nervous system.

Therapeutic compositions which contain at least one compound of the formula I or one of its non-toxic addition salts as the active ingredient, in combination with a physiologically acceptable excipient, are within the scope of the invention.

I claim:
1. A phenylsulphinyl derivative of the formula:

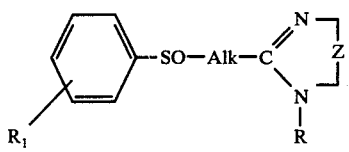

in which $R_1$ is a substituent selected from the group consisting of H, F, Cl, Br, $CF_3$, $C_1$-$C_4$ alkyl, $C_1$-$C_4$ alkoxy and $NO_2$, Alk represents a $C_2$-$C_4$ hydrocarbon radical having a linear or branched chain, Z is selected from the group consisting of $CH_2CH_2$ and $CH_2CH_2CH_2$ and R is selected from the group consisting of H, $CH_2COOH$ and $C(CH_3)_2COOH$ and non-toxic acid addition salts thereof.

2. A phenylsulphinyl derivative as claimed in claim 1 wherein $R_1$ is selected from the group consisting of H, F, Cl, and $CF_3$ and Alk is selected from the group consisting of $CH_2CH_2$ and $CH_2CH_2CH_2$.

3. A phenylsulphinyl derivative as claimed in claim 1 which is 2-[2-(p-chlorophenylsulphinyl)-ethyl]-$\Delta^2$-imidazoline hydrochloride.

4. A phenylsulphinyl derivative as claimed in claim 1 which is 2-[2-(meta-tifluoromethylphenylsulphinyl)-ethyl]-$\Delta^2$-imidazoline hydrochloride.

5. A phenylsulphinyl derivative as claimed in claim 1 which is 2-[2-(phenylsulphinyl)-ethyl]-$\Delta^2$-imidazolin-1-yl -acetic acid.

6. A phenylsulphinyl derivative as claimed in claim 1 which is {2-[2-(p-chlorophenylsulphinyl)-ethyl]-$\Delta^2$-imidazolin1-yl}-acetic acid.

7. A phenylsulphinyl derivative as claimed in claim 1 which is $\alpha$-{2-[2-(p-chlorophenylsulphinyl)-ethyl]-$\Delta^2$-imidazolin1-yl}-propionic acid.

8. A phenylsulphinyl derivative as claimed in claim 1 which is 2-[2-(phenylsulphinyl)-ethyl]-$\Delta^2$-imidazoline hydrochloride.

* * * * *